United States Patent [19]
Fozzard

[11] 4,092,257
[45] May 30, 1978

[54] CONSTANT BOILING ADMIXTURES OF TOLUENE/PERFLUORO-N-HEPTANE

[75] Inventor: George B. Fozzard, Bartlesville, Okla.

[73] Assignee: Phillips Petroleum Company, Bartlesville, Okla.

[21] Appl. No.: 765,516

[22] Filed: Feb. 4, 1977

Related U.S. Application Data

[62] Division of Ser. No. 625,742, Oct. 24, 1975, Pat. No. 4,029,552.

[51] Int. Cl.² .......................... H01B 3/24; C23G 5/02; C11D 7/30

[52] U.S. Cl. ........................................ 252/66; 134/40; 252/162; 252/364; 252/DIG. 9

[58] Field of Search ................. 252/162, 364, DIG. 9, 252/66; 134/40; 260/648 F, 652 P, 653; 203/68, 69

[56] References Cited

U.S. PATENT DOCUMENTS

| | | | |
|---|---|---|---|
| 2,789,087 | 4/1957 | Cines | 203/59 X |
| 4,029,552 | 6/1977 | Fozzard | 203/69 |

Primary Examiner—Harris A. Pitlick

[57] ABSTRACT

Toluene/perfluoro-n-heptane mixtures, and employment thereof in the purification of perfluoro-n-heptane.

7 Claims, 1 Drawing Figure

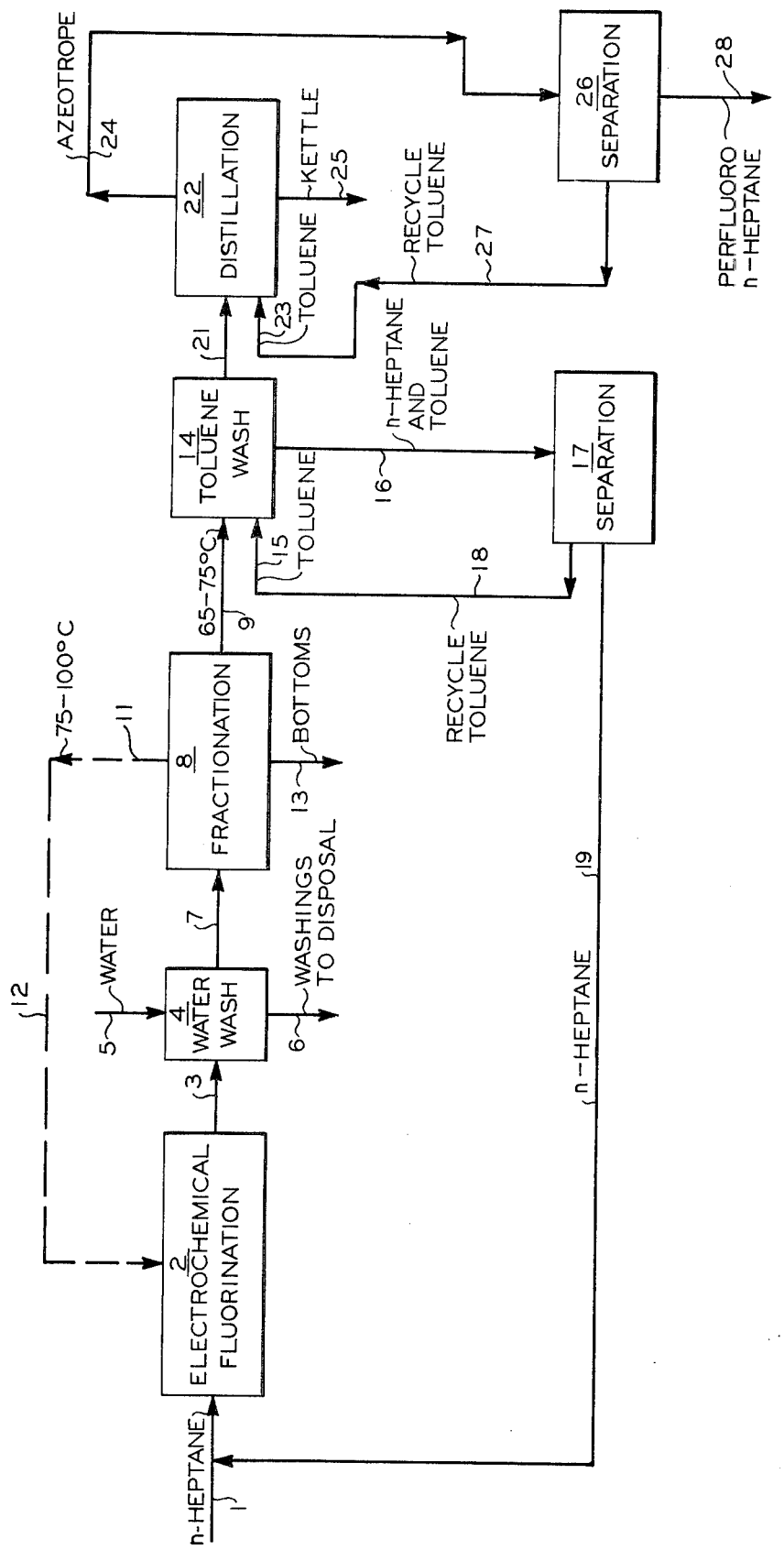

4,092,257

CONSTANT BOILING ADMIXTURES OF TOLUENE/PERFLUORO-N-HEPTANE

This is a divisional application of Ser. No. 625,742 filed Oct. 24, 1975, now U.S. Pat. No. 4,029,552 patented June 14, 1977.

FIELD OF THE INVENTION

The invention relates to a novel composition of toluene and perfluoro-n-heptane. In another aspect, the invention relates to a method of purification of perfluoro-n-heptane.

BACKGROUND OF THE INVENTION

The electrochemical fluorination of n-heptane provides a product mixture containing perfluoro-n-heptane (hexadecafluoroheptane), hydrogen fluoride, n-heptane, and a variety of intermediates of varying degree of fluorination. The perfluoro-n-heptane is a potentially valuable product, were it feasible to economically recover the material as a relatively pure product.

Electrochemical Fluorination

The electrochemical fluorination of n-heptane is conducted by a process wherein current-conducting essentially anhydrous liquid hydrogen fluoride electrolyte is electrolyzed in an electrolysis cell provided with a cathode and a porous anode. The fluorinatable organic compound, which for the production of perfluoro-n-heptane and can comprise partially fluorinated heptanes, is introduced into the pores of the anode wherein a portion of the fluorinatable organic compound is at least partially fluorinated, and thereafter fluorinated products can be recovered from the cell. Suitable methods of electrochemical fluorination are described in such patents as U.S. Pat. No. 3,511,761 issued May 12, 1970, to W. V. Childs and F. N. Ruehlen; U.S. Pat. No. 3,806,432 issued Apr. 23, 1974, to K. L. Mills; and U.S. Pat. No. 3,511,760 issued May 12, 1970, to H. M. Fox and F. N. Ruehlen.

The electrochemical fluorination of n-heptane provides a product mixture containing unreacted n-heptane, a variety of partially fluorinated heptanes, some by-products of fluorination such as hydrogen fluoride, and broadly about 5 to 10 percent, more usually about 3 to 7 weight percent, perfluoro-n-heptane.

BRIEF DESCRIPTION OF THE DRAWING

In the figure, n-Heptane 1 is subjected to electrochemical fluorination 2. The electrochemical cell product effluent 3 preferably is water washed 4 with water 5 to remove water-soluble acidic components. The water washings are discarded 6 or otherwise disposed of. The water-washed product stream 7 is fractionated to produce a first overhead fraction 9 boiling from about 65° to about 75° C, a second overhead fraction 11 boiling from about 75° to 100° C, and a bottoms product 13 of material boiling over about 100° C. The bottoms product 13 is discarded. The higher boiling fraction 11 can be recycled 12 to electrochemical fluorination 2. The first overhead fraction 9 is toluene washed 14 employing toluene 15. A resulting stream of toluene and n-heptane 16 is separated 17 to produce recycle toluene 18 and recycle n-heptane 19. The washed product stream 21 is distilled 22 with excess toluene 23, producing an azeotrope overhead 24 of toluene/perfluoro-n-heptane, and a kettle product of excess toluene and impurities. The excess toluene in stream 25 can be separated (not shown), such as by distillation for recycle, and residual kettle product of partially fluorinated products can be returned (not shown) for electrochemical fluorination. The azeotrope 24 is separated to obtain toluene 27, which can be recycled as desired, and substantially pure perfluoro-n-heptane 28.

DESCRIPTION OF THE INVENTION

According to the process of my invention, pure perfluoro-n-heptane can be isolated from the cell product effluent stream from the electrochemical fluorination of n-heptane by use of a novel toluene/perfluoro-n-heptane constant boiling mixture.

The total cell product effluent preferably is first water washed to remove water soluble acidic components particularly hydrogen fluoride. The water washings with hydrogen fluoride can be discarded or sent to acid waste disposal.

The water-washed product stream from the electrochemical fluorination cell comprising perfluoro-n-heptane, unreacted n-heptane, and a variety of partly fluorinated materials, then is fractionated. The first overhead fraction boiling from about 65° to 75° C at ambient substantially atmospheric pressure contains n-heptane, perfluoro-n-heptane, and a variety of partly fluorinated heptanes.

The second overhead fraction, boiling at about 75° to 100° C, largely represents partially fluorinated heptanes and contains less than about 1 percent perfluoro-n-heptane. This fraction of lesser or partially fluorinated heptanes can be recycled, if desired, to the electrochemical cell for further fluorination. The bottoms product, comprising material not distilling below about 100° C., presently is discarded, since attempts at distillation thereof tend to result in decomposition with evolution of HF.

The n-heptane/perfluoro-n-heptane first fraction is washed with toluene, preferably several portions, so as to remove most of the n-heptane. Perfluorinated hydrocarbons are only slightly soluble in toluene so that such an extraction step removes almost all of the n-heptane with only very slight loss of perfluoro-n-heptane. The toluene/n-heptane washings can be readily fractionated to recover a separated toluene fraction for recycle to the toluene treatment step, and a separated n-heptane fraction which can be recycled to the electrochemical fluorination process.

The perfluoro-n-heptane raffinate from the toluene washing step, comprising perfluoro-n-heptane and a variety of partially fluorinated isomers of principally $C_7HF_{15}$ composition, is distilled with an excess volume, preferably about twice its volume, of toluene.

The distillation produces a first fraction of substantially pure toluene/perfluoro-n-heptane constant boiling mixture exhibiting the characteristics of an azeotrope and boiling at about 73°–74° C at substantially atmospheric pressure. The excess toluene and virtually all of the partially fluorinated impurities remain in the kettle. The toluene can be recovered by further distillation at suitable elevated temperature. The residual kettle product of partially fluorinated products can be returned for electrochemical fluorination, if desired.

The constant boiling toluene/perfluoro-n-heptane azetrope fraction comprises about 25 mol percent (10 weight percent) toluene and 75 mol percent (90 weight percent) perfluoro-n-heptane. This fraction can be readily resolved and the azeotropic components separated. The azeotrope exists in two phases even at room temperature. The phases can be separated at room temperature giving an upper toluene rich phase and a lower perfluoro-n-heptane rich phase. The toluene remaining in the lower phase is removed by topping the minimum boiling inventive azeotrope from the separated lower phase.

Cooling of the two phase azeotrope before phase separation is helpful but did not effect any dramatic improvement in the ultimate purity of the perfluoro-n-heptane. Where cooling is employed, the temperature of the mixture is reduced to a temperature of at least about $-10°$ C. or below, wherein the solubility of perfluoro-n-heptane in toluene is on the order of only about 2 percent.

The toluene separates into an upper layer which can then be separated, such as by drawing off, and discarded or recycled to the toluene wash step or distillation step. Toluene remaining in the now toluene-depleted perfluoro-n-heptane/toluene admixture then can be readily removed by distilling off the minimum boiling toluene/perfluoro-n-heptane azeotrope until the toluene is depleted in the kettle. The remaining kettle product so obtained is a high purity perfluoro-n-heptane with less than about 1 weight percent $C_7HF_{15}$ isomers.

EXAMPLES

The following data are supplied to illustrate the advantages and usefulness of my invention in the separation of perfluoro-n-heptane from a crude n-heptane electrochemical fluorination (ECF) product admixture. Examples I and II describe the preliminary treatment of the crude ECF product prior to using the novel toluene/n-$C_7F_{16}$ azeotrope in Examples III–V for purification.

EXAMPLE I

To a 1-liter distillation flask was added 520 g of crude n-heptane fluorination product which had been water-washed to remove water-soluble acidic components. The flask was fitted to a ¾ inch × 2 feet silvered, vacuum jacketed distillation column packed with 0.175 inches Heli-Pak. A water cooled, vacuum jacketed, magnetic takeoff head was attached to the column. Boil up was controlled by a powerstat through a heating mantel. The system was allowed to equilibrate for 30 min after reflux commenced. Distillation was at substantially atmospheric pressure.

TABLE I

| Cut | Head Temp., ° C. | Kettle Temp., ° C. | Reflux Ratio | Wt., g |
|---|---|---|---|---|
| 1 | 67.8/74.0 | 89.5/90.0 | 20:1/10:1 | 21.3 |
| 2 | 74.0/>100 | 90/140 | 20:1 | 413.8 |
| Kettle | | | | 78.8 |
| Trap | | | | 1 |
| Recovered | | | | 514.9 |
| Charge | | | | 520 |
| Loss | | | | 5.1 |

The kettle product was strongly acidic. Cut 1 was analyzed by GLC on a 3/16 inch × 12 feet 15% tris(cyanoethoxy)propane column at 35° C. The analysis in area percent was 39% $C_7F_{16}$, 26% $C_7H_{16}$, 35% other material. Cut 2 was recycled to the fluorination cell.

Example I demonstrates that distillation of the electrochemical fluorination cell effluent gave a fraction of material which was only 39 area percent of the desired perfluoro-n-heptane (n-$C_7F_{16}$).

EXAMPLE II

Extraction of Perfluoro-n-heptane Concentrate with Toluene

Cut 1 (21.3 g) from the previous distillation as described in Example I was washed twice with equal volumes of toluene in a small separatory funnel. The toluene upper layer was discarded and the fluorocarbon lower layer analyzed on a 12 feet × 3/16 inch 15% tris(cyanoethoxy)propane GLC column. Column temperature was held at 35° C. for 4 minutes and then programmed at 20° C./min. to 150° C. Analysis is reported as area percent.

TABLE II

| | $C_7F_{16}$ | $C_7H_{16}$ | Other | Toluene |
|---|---|---|---|---|
| Analysis excluding toluene, area % | 54 | 5.5 | 40.5 | — |
| Analysis including toluene, area % | 52 | 5 | 39 | 5 |

Example II demonstrates that a room temperature toluene extraction of the distillate from Example I removed a large percentage of the n-heptane, i.e., the area percent n-heptane was reduced from about 26 to about 5. Distillation of this toluene extracted material did not give rise to a high purity perfluoro-n-heptane sample.

EXAMPLE III

Distillation of Toluene Washed Perfloro-n-heptane Concentrate with Added Toluene A 125 theoretical plate spinning band column was used to distill 66 g of perfluoro-n-heptane with added toluene. The fluorocarbon (lower) layer of each cut was analyzed on a 12 feet × 3/16 inch 15% tris(cyanoethoxy)propane GLC column. Column temperature was held at 35° C. for 4 minutes and then programmed at 20° C./min. to 150° C.

TABLE III

| Cut | Head Temp. ° C. | Reflux Ratio | GLC Area % (lower layer) | | |
|---|---|---|---|---|---|
| | | | $C_7F_{16}$ | Other* | Toluene |
| 1 | 69/70 | 20:1 | 97.6 | 2.4 | |
| | | | 92.1 | 2.3 | 5.6 |
| 2 | 70/71 | 20:1 | 97.3 | 2.7 | |
| | | | 92 | 2.6 | 5.6 |
| 3 | 71/75 | 20:1 | 86 | 14 | |
| | | | 78 | 12 | 10 |
| 4 | 75/76 | 20:1 | 2.5 | 97.5 | |
| | | | 2 | 84 | 14 |
| Kettle | | | | | 98% |
| Starting Mixture | | | 78 | 22 | |

*Other was comprised principally of $C_7HF_{15}$ isomers.

The results in Example III demonstrate that the level of purity of the n-$C_7F_{16}$ was increased to 92.1 area percent by taking the toluene/perfluoro-n-heptane azeotrope overhead in cuts 1 and 2 of Table III. Cuts 3 and 4 are less rich in n-$C_7F_{16}$ because insufficient toluene and/or n-$C_7F_{16}$ remained in the kettle to sustain distillation of the minimum boiling toluene/n-$C_7F_{16}$ azeotrope.

EXAMPLE IV

Distillation of Purified Perfluoro-n-heptane to Remove Toluene

To a 125 theoretical plate spinning band column was charged a sample of 115 g purified perfluoro-n-heptane which had been accumulated from repeating the procedures of Examples I–III. Said sample contained approximately 5 mol percent toluene. The mixture was distilled until the head temperature had risen from 68° to 75° C. and 7.9 g of azeotropic material had been taken overhead. At this point the distillation was terminated and the 105 g of kettle product was analyzed on a 12 feet × 3/16 inch 15% tris(cyanoethoxy)propane GLC column. Column temperature was held at 35° C. for 4 minutes and then programmed at 20° C./min to 150° C. The kettle product was found to be 98.7 area percent perfluoro-n-heptane with the principal impurities being $C_7HF_{15}$ isomers.

The n-$C_7F_{16}$ material can be further purified to 99.0 to 99.5 weight percent perfluoro-n-heptane by repeating the azeotropic distillation with toluene. The lower n-$C_7F_{16}$ rich layer thus obtained is separated and the procedure of Example IV repeated to give a kettle product of 99.0 to 99.5 weight percent n-$C_7F_{16}$.

In the course of my work on the purification of perfluoro-n-heptane, as described hereinabove, I discovered a minimum boiling azeotrope of toluene and perfluoro-n-heptane. I discovered that these materials form an azeotrope with a boiling point of about 73° to 75° C at substantially ambient atmospheric pressure which azeotrope contains about 25 mol percent toluene (10 weight percent)/75 mol percent perfluoro-n-heptane (90 weight percent), which has usefulness in the purification of perfluoro-n-heptane admixtures as described hereinabove.

In order to confirm this azeotropic composition, distillations were carried out in which the original kettle composition was richer, or poorer, in toluene than the azeotrope discovered.

EXAMPLE V

A mixture of 24 g (0.26 mol) toluene and 120 g of a commercial sample of perfluoro-n-heptane containing about 85 weight percent $C_7F_{16}$ and about 15 weight percent of partially fluorinated heptanes was charged to a laboratory distillation flask fitted with a vacuum jacketed spinning band distillation column, condenser, and receiver. The original kettle composition contained about 16.6 weight percent toluene and about 71 weight percent perfluoro-n-heptane. The external surface of the vacuum jacketed column was maintained about 10° to 15° C. higher than the distillation temperature so as to minimize heat losses. The mixture was heated to boiling temperatures at atmospheric pressure and a distillate collected which weighed 70.15 grams. During collection of this distillate, the pot temperature was about 73° C., and the head temperature about 74° C. The 78.15 gram distillate was composed of an upper toluene-rich layer. 7.6 grams, and a lower perfluoro-n-heptane-rich phase, 70.55 grams. The pot residue on cooling to room temperature separated into an upper toluene-rich layer of 14.6 grams, and a lower fluorocarbon-rich layer of 34.8 grams. The toluene/perfluoro-n-heptane azeotrope, 78.15 gram distillate above, then was characterized by gas chromatographic analysis with the results as shown below in Table IV:

TABLE IV

| | Toluene/Perfluoro-n-heptane Azeotrope (Original Kettle Composition Richer in Toluene than the Azeotrope) | | | | |
|---|---|---|---|---|---|
| | Glc Area % | Glc[a] Wt. % | Phase Wt. (g) | Total Wt. of Components in Distillate[b] | Azeotropic Composition Wt. % |
| | $C_7F_{16}$ $C_7H_8$ | $C_7F_{16}$ $C_7H_8$ | | $C_7F_{16}$ $C_7H_8$ | $C_7F_{16}$ $C_7H_8$ |
| Upper Layer | 0.77 99.23 | 1.98 98.02 | 7.6 | | |
| | | | | 69.25 8.90 | 88.6 11.4 |
| Lower Layer | 94.8 5.2 | 97.93 2.07 | 70.55 | | |

[a]Calculated from "Glc Area %" by the use of response factors derived from data on synthetic blends of toluene and perfluoro-n-heptane.
[b]Calculated by multiplying "Phase Wt. (b)" by "Glc Wt. %".

These data confirm the azeotropic composition at 88.6 weight percent perfluoro-n-heptane/11.4 weight percent toluene. This is characterized according to distillation data obtained, as having a boiling point of about 73°–75° C at ambient substantially atmospheric pressure.

EXAMPLE VI

A further run was made employing a kettle composition of about 5 weight percent toluene and 95 weight percent perfluoro-n-heptane. A 70.5 gram portion of this mixture was fractionated similarly as described in Example II above. The minimum boiling azeotrope boiling at about 73° C. at ambient substantially atmospheric pressure was then characterized by gas chromatographic analysis to give results as shown below in Table V:

TABLE V

| | Toluene/Perfluoro-n-heptane Azeotrope (Original Kettle Composition Poorer in Toluene than the Azeotrope) | | | | |
|---|---|---|---|---|---|
| | Glc Area % | Glc[a] Wt. % | Phase Wt. (g) | Total Wt. of Components in Distillate[b] | Azeotropic Composition Wt. % |
| | $C_7F_{16}$ $C_7H_8$ | $C_7F_{16}$ $C_7H_8$ | | $C_7F_{16}$ $C_7H_8$ | $C_7F_{16}$ $C_7H_8$ |
| Fraction I | | | | | |
| Upper Layer | 1.16 98.84 | 2.96 97.04 | 1.03 | | |
| | | | | 14.26 1.42 | 90.9 9.1 |
| Lower Layer | 92.83 7.17 | 97.11 2.89 | 14.65 | | |
| Fraction II | | | | | |
| Upper Layer | 0.99 99.1 | 2.53 97.47 | 1.2 | | |

TABLE V-continued

Toluene/Perfluoro-n-heptane Azeotrope
(Original Kettle Composition Poorer in Toluene than the Azeotrope)

|  | Glc Area % | Glc[a] Wt. % | Phase Wt. (g) | Total Wt. of Components in Distillate[b] | Azeotropic Composition Wt. % |
|---|---|---|---|---|---|
|  |  |  |  | 13.24  1.42 | 89.9  10.1 |
| Lower Layer | 94.07  5.93 | 97.63  2.37 | 13.53 |  |  |

[a] As defined in Table I.
[b] As defined in Table I.

The above data illustrate the existence of the toluene/perfluoro-n-heptane azeotrope, and the fact that it can be obtained in distillation of a kettle composition poorer in toluene than the azeotrope.

EXAMPLE VII

In this run, a mixture was prepared of toluene, perfluoro-n-heptane, and a lower layer of the kettle bottoms product from Example II above. A 23.8 gram (0.26 mole) sample of toluene, together with 34.8 grams of a lower kettle product layer from Example II above, and a 12 gram sample of perfluoro-n-heptane (99.39 area percent pure according to GLC analysis) were charged together to a distillation flask fitted with an efficient spinning band distillation column of 125 theoretical plates, condenser, and receiver. This mixture was heated to boiling at a pressure of 747 millimeters mercury, and a two-phase distillate then was collected at a head temperature of approximately 75° C. 16.1 grams of the two-phase fraction were characterized by gas chromatographic analysis to give results as shown in Table VI:

Table VI

Toluene/Perfluoro-n-heptane Azeotrope

|  | Glc Area % | | Glc[a] Wt. % | | Phase Wt. (g) | Total Wt. of Components in Distillate[b] | | Azeotropic Composition Wt. % | |
|---|---|---|---|---|---|---|---|---|---|
|  | $C_7F_{16}$ | $C_7H_8$ | $C_7F_{16}$ | $C_7H_8$ |  | $C_7F_{16}$ | $C_7H_8$ | $C_7F_{16}$ | $C_7H_8$ |
| Upper Layer | 0.96 | 99.04 | 2.46 | 97.54 | 1.1 |  |  |  |  |
|  |  |  |  |  |  | 14.61 | 1.49 | 90.7 | 9.3 |
| Lower Layer | 93.12 | 6.88 | 97.23 | 2.77 | 15.0 |  |  |  |  |

[a] As defined in Table I.
[b] As defined in Table I.

A constant boiling mixture which distills without changing composition is defined as an azeotrope. Yet, at a differing pressure, the composition indeed may vary, at least slightly, with the change in distillation pressure, which also changes, at least slightly, with distillation temperature. Thus, an azeotrope of A and of B may represent a unique type of relationship with a variable composition. This fact is illustrated by the data above.

Thus, it is feasible to fingerprint, in effect, a constant boiling mixture which may appear under varying guises, depending on the conditions chosen, by any of several criteria: The composition may be defined as an azeotrope of A and B, since the very term "azeotrope" is at once definitive and limitative requiring that A and B indeed form this unique composition of matter which is a constant boiling type of mixture. Or, the composition may be defined as a particular weight percent relationship or mol percent relationship of A:B, but recognizing that such a value point out only one particular such relationship, while in actuality a series of such relationships A:B actually may exist for an azeotrope, varied by influence of temperature and pressure. Or, recognizing that broadly speaking, an azeotrope of A:B actually represents just such a series of relationships, the azeotropic series represented by A:B may in effect be fingerprinted or characterized by defining the composition as an azeotrope further characterized by a particular boiling point at a given pressure, thus giving identifying characteristics without induly limiting the scope of the discovery.

The constant boiling mixture which I have discovered containing perfluoro-n-heptane/toluene is characterized as about 75 mole % (90 weight percent) perfluoro-n-heptane and correspondingly about 25 mole % (10 weight percent) toluene. The mixture exhibits the characteristics of an azeotrope. The weight relationship and boiling point vary somewhat; as the atmospheric pressure varies, from about 88.6 to 90.9 perfluoro-n-heptane and 11.4 to 9.1 toluene at 73°–75° C. Values obtained on distillation include weight percent relationships as shown in the Examples above.

Of course, it would be improper to so strictly define azeotropes by exacting percentage compositions for reasons as discussed above, due to possibly slight variations in accuracy of monitoring analytical equipment.

When analyzing cuts of a distillate to determine approximate compositions, it is recognized that specific temperature:pressure relationships govern particular compositions at a given time.

A constant boiling mixture which I have discovered is useful in purification of perfluoro-n-heptane from electrochemical fluorination product mixtures derived from the electrochemical fluorination of n-heptane. In addition, my azeotrope has utility in application as a vapor degreasing solvent, and also as cleaning solvents for various purpose such as for garments and the like.

The product recovered according to my process, the perfluoro-n-heptane itself, has utility as a liquid dielectric and as a blood substitute.

The disclosure, including data, illustrate the value and effectiveness of my invention. The examples, the knowledge and background of the field of the invention, and general principles of chemistry and other applicable sciences, have formed the bases from which the broad descriptions of the invention including the ranges of conditions have been developed, and which form the bases for my claims as here appended.

I claim:

1. A substantially constant boiling mixture of (A) perfluoro-n-heptane and (B) toluene, characterized by a weight percent ratio of about 88.6–90.9 (A):11.4–9.1 (B) at substantially atmospheric pressure.

2. The substantially constant boiling mixture according to claim 1 characterized by a boiling point of about 73° to 75° C at substantially atmospheric pressure.

3. The substantially constant boiling mixture according to claim 1 further characterized as an azeotrope and a weight percent ratio of about 88.6 (A) and 11.4 (B).

4. The substantially constant boiling mixture according to claim 1 further characterized as an azeotrope and a weight percent ratio of about 89.9 (A) and 10.1 (B).

5. The substantially constant boiling mixture according to claim 1 further characterized as an azeotrope and a weight percent ratio of about 90.9 (A) and 9.1 (B).

6. The substantially constant boiling mixture according to claim 1 further characterized as an azeotrope and a weight percent ratio of about 90.7 (A) and 9.3 (B).

7. A binary azeotrope of perfluoro-n-heptane and toluene characterized by a relationship of about 75 mol percent perfluoro-n-heptane and 25 mol percent toluene at a boiling point of about 73° to 75° C at substantially atmospheric pressure.

* * * * *